United States Patent [19]

Guziec, Jr.

[11] 4,399,281
[45] Aug. 16, 1983

[54] 2,2'-BIPYRIDINIUM CHLOROCHROMATE OXIDANT

[75] Inventor: Frank S. Guziec, Jr., Las Cruces, N. Mex.

[73] Assignee: Thiokol Corporation, Chicago, Ill.

[21] Appl. No.: 304,456

[22] Filed: Sep. 22, 1981

[51] Int. Cl.$^3$ .................... C07B 3/00; C07D 401/04; C07D 333/16; C07D 317/54
[52] U.S. Cl. .......................... 546/9; 549/78; 549/454; 568/322; 568/363; 568/426; 568/483
[58] Field of Search ............................................ 546/9

[56] References Cited

U.S. PATENT DOCUMENTS 4,241,098  12/1980  Mussinan et al. .................. 568/421
4,282,154   8/1981  Lischewski et al. .................... 71/89

OTHER PUBLICATIONS

Chakraborty et al., Chem. Ab., 94, 174249u.
Anantakrishnan et al., Ind. J. Chem. 2, 146 (1964).
Rios et al., Chem. Abs. 68, 83915e.
Trujillo et al., Chem. Abs. 78, 89240; (1972).
Corey, E. J. and Suggs, J. W., *Pyridinium Chlorochromate, A Efficient Reagant for Oxidation of Primary and Secondary Alcohols to Carbonyl Compounds*, Tetrahedron Letters No. 31, pp. 2647-2650, 1975.

*Primary Examiner*—Mark L. Berch
*Attorney, Agent, or Firm*—Gerald K. White; Richard J. Sheridan

[57] ABSTRACT

2,2'-Bipyridinium chlorochromate has been found to be an effective oxidizing agent, particularly for the conversion of primary or secondary alcohols to their respective aldehydes or ketones.

1 Claim, No Drawings

2,2'-BIPYRIDINIUM CHLOROCHROMATE OXIDANT

BACKGROUND OF THE INVENTION

Chromium (VI) reagents have been widely used in organic chemistry for the oxidation of primary and secondary alcohols to carbonyl compounds. Pyridine-chromium trioxide complexes and pyridinium chlorochromate have been especially useful reagents for the mild oxidation of primary alcohols to aldehydes. There are, however, some significant difficulties associated with the reagents. For instance, chromium containing by-products often contaminate the desired products, requiring time consuming purifications. Also, polymeric, chromium containing tars are formed which contaminate both the reaction and work-up apparatus.

SUMMARY OF THE INVENTION

A novel compound 2,2'-bipyridinium chlorochromate, has been discovered which is useful as an oxidizing agent. The compound is especially useful as an oxidizing agent in reactions which require relatively mild oxidizing conditions, such as the conversion of primary or secondary alcohols to carbonyl compounds.

Thus, in accordance with this invention there is provided the compound 2,2'-bipyridinium chlorochromate.

In accordance with this invention there is also provided a process for oxidizing a primary or secondary alcohol to the corresponding carbonyl compound by reacting the alcohol and 2,2'-bipyridinium chlorochromate.

BRIEF DESCRIPTION OF THE PREFERRED EMBODIMENTS

The compound of this invention, 2,2'-bipyridinium chlorochromate, has the following structure:

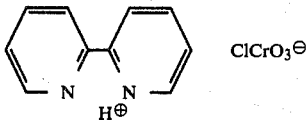

and, for convenience, will sometimes be referred to herein as Bipy.HCrO$_3$Cl.

The Bipy.HCrO$_3$Cl may be readily prepared by adding, at room temperature, commercially available 2,2'-bipyridine to a mixture containing equimolar amounts of chromic anhydride and dilute hydrochloric acid. The resulting product is a yellow crystalline complex which is non-hygroscopic and air-stable.

The Bipy.HCrO$_3$Cl of this invention is useful as an oxidizing agent, especially for those reactions which require mild oxidizing conditions. Thus, in the practice of the process of this invention, a primary or secondary alcohol may be converted to the corresponding carbonyl compound by reacting the primary or secondary alcohol and Bipy.HCrO$_3$Cl at a molar ratio of alcohol to Bipy.HCrO$_3$Cl of about 1:2 to about 1:4 in a suitable solvent such as, for example, dichloromethane or acetone. The particular reaction conditions, i.e. reaction temperature, reaction time and the like, will, of course, vary depending upon the particular alcohol employed. The resulting product is a solution containing the desired carbonyl compound and a water soluble, crystalline chromium containing by-product which may be completely removed from the product by filtration. A dilute acid wash, to remove traces of 2,2'-bipyridine, and removal of the solvent yields the desired carbonyl compound, which may be further purified if desired by standard techniques known in the art, in excellent yields.

The process of this invention may be illustrated by, but not limited to, the following reactions.

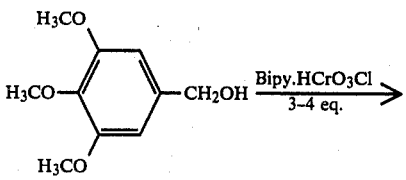

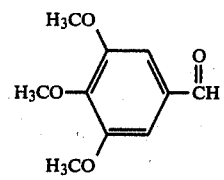

typical yield = 68–85%

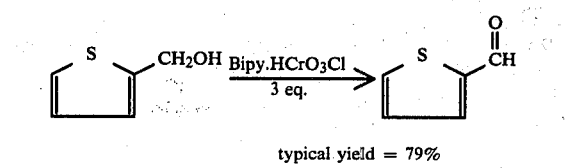

typical yield = 79%

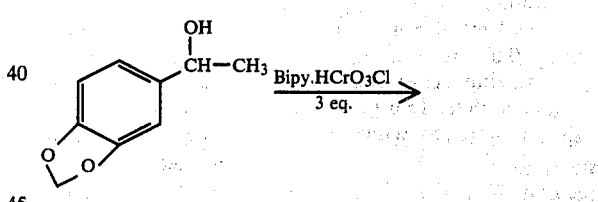

typical yield = 95%

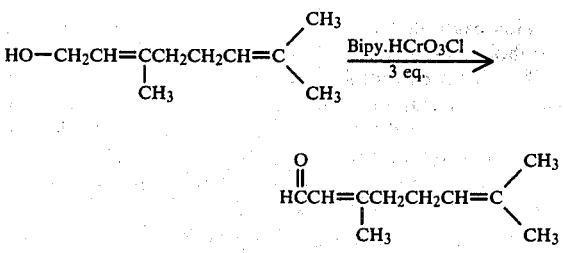

typical yield = 93%

-continued

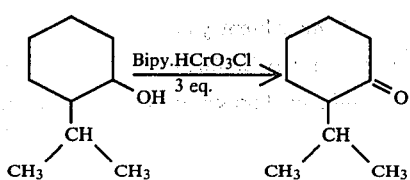

typical yield = 86%

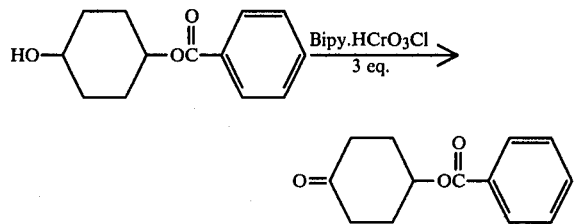

typical yield = 83%

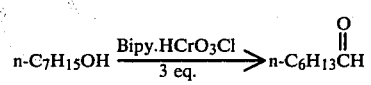

typical yield = 82%

The following examples further illustrate the invention, and it will be understood that the invention is not limited thereto. In the examples, and throughout this specification, all parts and percentages are by weight unless otherwise specified.

EXAMPLE 1

This example illustrates the preparation of 2,2'-bipyridinium chlorochromate.

To 18.4 ml of 6 M hydrochloric acid (0.11 mole) is added 10.0 g. (0.11 mole) of chromium trioxide rapidly while stirring. After dissolution of the chromium trioxide is complete, 15.6 g. (0.1 mole) of 2,2'-bipyridine is added in portions while stirring vigorously. A yellow slurry results which is stirred for 1 hour at room temperature. The slurry is then collected on a sintered glass funnel and washed with two 15 ml portions of cold distilled water. The resulting solid yellow filter cake is dried for 3 hours in vacuo at room temperature. The resulting product is 2,2'-bipyridinium chlorochromate, and is obtained in a typical yield of 26.8 g. which is 92% of the theoretical yield. The product is analyzed with the following results:

Theoretical: C—41.04%; H—3.10%; N—9.57%; Cl—12.10%; Cr—17.77%, Found: C—40.90%; H—3.18%; N—9.49%; Cl—12.40%; Cr—17.50%.

EXAMPLE 2

This example illustrates the conversion of cinnamyl alcohol to cinnamaldehyde.

To 10 ml of dichloromethane is added 0.5 g. (3.73 mmoles) of cinnamyl alcohol. The resulting mixture is added to a stirred suspension of 3.37 g. (11.5 mmoles) of 2,2'-bipyridinium chlorochromate in 15 ml of dichloromethane. The resulting mixture is stirred for four hours after which 15 ml of anhydrous ether is added. The resulting product is filtered through a Hirsch funnel packed 1-2 cm deep with Celite ® using ether as a wash solvent. The resulting clear filtrate is washed with 5% hydrochloric acid and 10% sodium carbonate, and dried over sodium sulfate. The drying agent is removed and the solvent evaporated giving a product which is a slightly yellow oil. This oil is then distilled via Kugelrohr to yield pure cinnamaldehyde in a typical yield of 0.323 g. which is 86% of theoretical yield.

EXAMPLE 3

This example illustrates the conversion of 2-isopropylcyclohexanol to 2-isopropylcyclohexanone.

To a suspension of 4.0 g. (13.7 mmole) of 2,2'-bipyridinium chlorochromate in 15 ml of dichloromethane is added, while stirring, 0.5 g. (3.5 mmole) of 2-isopropylcyclohexanol in 10 ml of dichloromethane. The resulting reaction mixture is stirred for 4 hours and then filtered through a Hirsch funnel packed with 2 cm of Celite ®. The resulting clear filtrate is washed with 5% hydrochloric acid and 10% sodium carbonate, and dried over magnesium sulfate. The drying agent is then removed and the solvent evaporated to yield a colorless oil which is distilled via Kugelrohr to yield pure 2-isopropylcyclohexanone in a typical yield of 0.425 g. which is 86% of theoretical yield.

EXAMPLES 4–13

The following alcohols are converted to their corresponding aldehyde or ketone in the yields indicated in Table I using the procedure of Example 1 and the conditions indicated in Table I.

TABLE I

| Example No. | Alcohol | Conditions Eq. of Bipy.HCrO$_3$Cl/ Reaction Time (Hrs)[a,b] | Yield (%)[c] |
|---|---|---|---|
| 4 | H$_3$CO—, H$_3$CO—⟨benzene⟩—CH$_2$OH, H$_3$CO | 4/3.5 | 68 |
| 5 | ⟨benzene⟩—CH$_2$OH | 2/2.5 | 79 |
| 6 | ⟨methylenedioxybenzene⟩—CH(OH)CH$_3$ | 3/3.5 | 95 |
| 7 | ⟨thiophene⟩—CH$_2$OH (S) | 3/3 | 79 |
| 8 | HO—⟨cyclohexyl⟩—OC(O)—⟨phenyl⟩ | ? | 83 |
| 9[d,e] | CH$_3$—C(=CH—CH$_2$OH)—CH$_2$—CH$_2$—CH=C(CH$_3$)$_2$ | 3/3 | 93 |

TABLE I-continued

| Example No. | Alcohol | Conditions Eq. of Bipy.HCrO3Cl/ Reaction Time (Hrs)[a,b] | Yield (%)[c] |
|---|---|---|---|
| 10 | 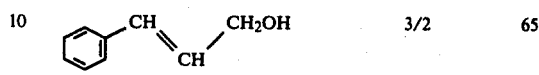 | 3/2 | 65 |
| 11 | 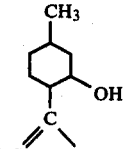 | 4/2 | —[f] |
| 12 | n-C$_{12}$H$_{25}$OH | 3/2 | 37 |
| 13 | n-C$_7$H$_{15}$OH | 2.5/2.5 | 82 |

[a] Dichloromethane used as the reaction solvent.
[b] 1–4 mmole of alcohol employed.
[c] Isolated yields of pure carbonyl compounds.
[d] G.L.C. analysis of the reaction mixture reveals that 6% isomerization about the double bond occurs. Under the same conditions, oxidation of the cis isomer results in a 90% conversion to the cis aldehyde.
[e] This conversion also done using acetone as the solvent, resulting in 89% conversion to the aldehyde.
[f] Conversion was 51%, no α,β-isomer (d,l-pulegone) was detected by G.L.C. analysis.

What I claim and desire to protect by Letters Patent is:

1. 2,2'-bipyridinium chlorochromate.